United States Patent [19]

Sharkawy

[11] Patent Number: 5,259,386
[45] Date of Patent: Nov. 9, 1993

[54] FLOW MONITOR AND VASCULAR ACCESS SYSTEM WITH CONTINUOUSLY VARIABLE FREQUENCY CONTROL

[75] Inventor: Ahmed Sharkawy, Mountain View, Calif.

[73] Assignee: Advanced Cardiovascular Systems, Inc., Santa Clara, Calif.

[21] Appl. No.: 901,466

[22] Filed: Jun. 19, 1992

[51] Int. Cl.$^5$ ............................................. A61B 8/00
[52] U.S. Cl. ........................... 128/662.04; 128/662.05; 128/662.03; 128/661.09
[58] Field of Search ................. 128/662.04, 662.05, 128/662.03, 661.08, 661.09

[56] References Cited

U.S. PATENT DOCUMENTS

| | | | |
|---|---|---|---|
| 4,097,835 | 6/1978 | Green | 128/662.04 |
| 4,413,629 | 11/1983 | Durley, III | 128/662.04 |
| 4,548,210 | 10/1985 | Enjoji et al. | 128/662.05 |
| 4,870,867 | 10/1989 | Shaulov | 128/662.05 |

Primary Examiner—William E. Kamm
Assistant Examiner—George Manuel
Attorney, Agent, or Firm—Dykema Gossett

[57] ABSTRACT

An apparatus for use in flow monitoring and cannulation of blood vessels which includes vascular accessing capabilities. The apparatus includes a flux panel, an audio monitor, and a probe-needle assembly. The flux panel is composed of two or more sections hingedly connected wherein each section includes a transducer having a continuously varying thickness from one end to the other. Successive bands of excitation are progressively created along the length of each transducer as different frequencies are transmitted thereto. The apparatus may be operated in either monitor or access modes with both manual and automatic changes in frequencies. The apparatus is capable of transmitting high-powered ultrasonic waves of continuously variable resonant frequencies to be used along with an audio monitor for sensing flow or in conjunction with a probe-needle assembly to locate body vessels.

14 Claims, 2 Drawing Sheets

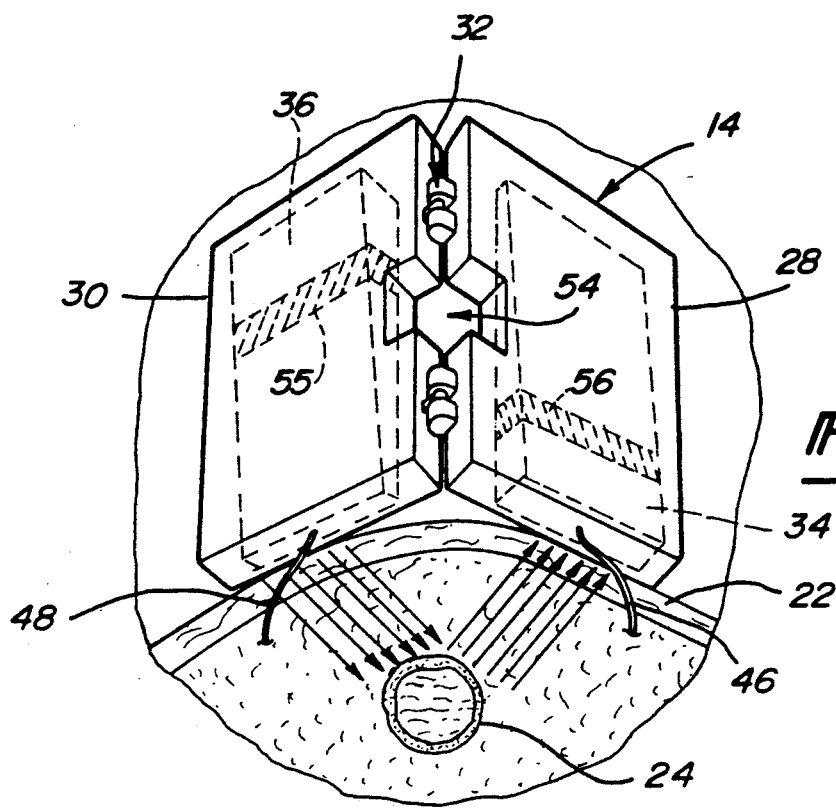
*Fig-3*
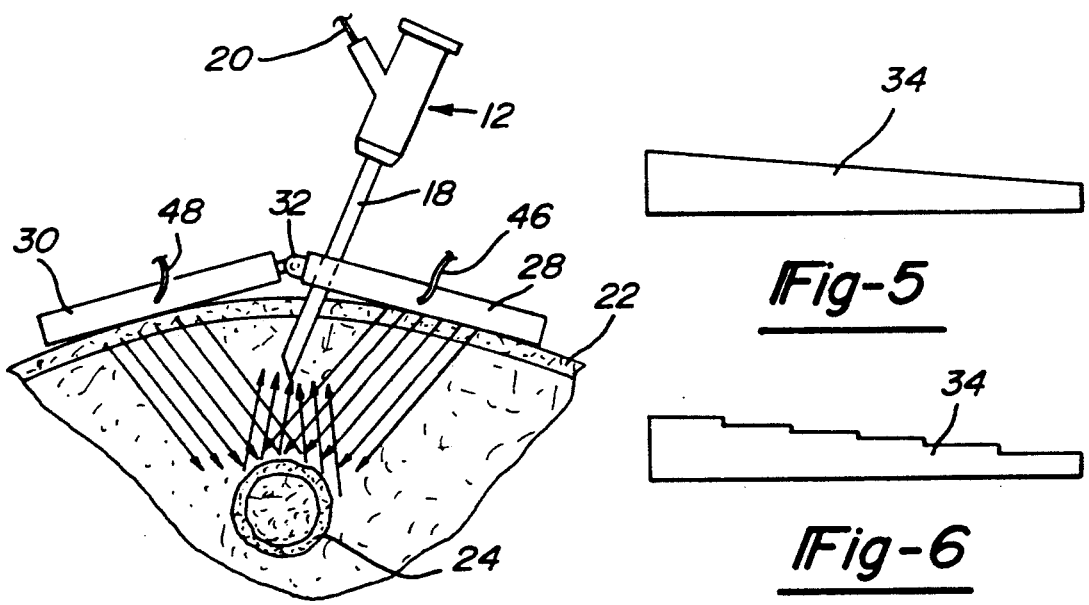
*Fig-4*
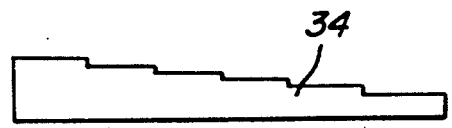
*Fig-5*
*Fig-6*
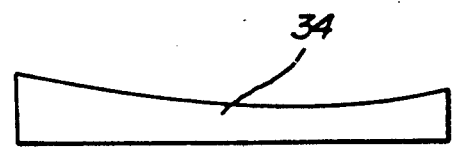
*Fig-7*

FLOW MONITOR AND VASCULAR ACCESS SYSTEM WITH CONTINUOUSLY VARIABLE FREQUENCY CONTROL

TECHNICAL FIELD OF THE INVENTION

The present invention relates generally to the cannulation of arteries and veins through the use of ultrasonic techniques.

BACKGROUND OF THE INVENTION

In many operating procedures, it is often necessary to introduce catheters into the large veins of the body and into the arterial vessel system. Arterial and venous catheters are particularly useful for cardiac catheterization and other radiologic procedures such as cerebral angiograms. It is well established that the insertion of arterial and venous catheters for various purposes such as for angiography can be responsible for patient discomfort because locating and penetrating arteries and veins can be especially difficult when dealing with patients who are obese or present an unusual anatomical situation.

Repeated attempts at penetration may be required for vessels which are difficult to reach. Multiple blind penetrations can cause injuries even extending to an occlusion of the vessel concerned. Further, frustrated attempts at penetration lead to loss of time, which is undesirable, for example, in the case of an emergency or even when preparing for an elective operation.

To avoid difficulties when localizing the vessel and to reduce the risk of complications, it is known to determine the position and the course of the vessel to be penetrated by means of ultrasonic Doppler sonography. A known apparatus emits an ultrasonic beam of a specific frequency from the skin surface toward the interior of the body. If any blood vessels are present within this ultrasonic beam, the emitted wave undergoes a Doppler effect due to flow through the blood vessels or the pulsation of the vascular walls, so that a reflected wave that has a different frequency from that of the emitted wave can be obtained.

After this reflected wave has been converted into an electrical signal with an ultrasonic oscillator, synthetic detection of the emitted signal allows an electric signal of the difference of the two waves to be obtained. This can be amplified and sent to a speaker or the like to produce a sound having a unique tone that can be detected by the ear. These sounds reach their maximum volume when the ultrasonic beam is directed toward the center of the artery or vein in question and cease if the ultrasonic beam strays from the vessel. Further, the reflected wave from tissue that has no movement cannot be heard nor can the sound resulting from vessels that are out of the line of the beam. Hence, Doppler sonography provides a simple means of localizing vessels both easily and accurately.

Certain applications of Doppler ultrasound utilize the transmission of ultrasonic waves through the needle and reception of ultrasonic echoes by a separate transducer located on the body of the patient separated from the syringe and needle. For example, U.S. Pat. No. 3,556,079 directed to a "Method of Puncturing A Medical instrument Under Guidance of Ultrasound" discloses an apparatus wherein an ultrasonic beam is transmitted through a needle and the backscattered waves which have changed their frequency in accordance with the Doppler effect are received by an apparatus located on the body of the patient away from the needle. This patent also discloses the placement of both the transmitting and receiving transducers in the needle and syringe. However, this requires a special catheter construction which may give an erroneous signal when the needle engages the blood vessel before penetrating the vessel.

A major advance to Doppler technology was made by virtue of U.S. Pat. No. 4,887,606 directed to an "Apparatus for Use In Cannulation of Blood Vessels", which teaches the use of a transducer insert positioned within a hollow needle including an ultrasonic transducer at one end for transmitting and receiving ultrasonic waves through the sharpened end of the needle. Upon location and penetration of a blood vessel, the transducer insert is removable from the needle for implementation of the known Seldinger technique for placing a catheter in a blood vessel. Although the device disclosed in U.S. Pat. No. 4,887,606, the disclosure of which is incorporated by reference herein, represents a superior apparatus for cannulation of blood vessels, such apparatus could be unproved upon. For example, the power emitted by a transmitting transducer is at least in part a function of surface area. Thus, larger surface area transducers can deliver more power and thereby increase the depth of penetration of the transmitted and reflected waves.

Since the reflected waves from small vessels that are located at large depths from the surface of the body are weak, it is important in certain applications to increase the depth of penetration of the transmitted and reflected waves. Moreover, with the known apparatus that utilizes a constant frequency transmission, it may be necessary to provide for somewhat sophisticated electronic amplification to sharpen the sensitivity of the receiving apparatus for the purpose of obtaining a strong detected sound. This obviously results in a more expensive and technically complicated receiving system. Therefore, there has been a need for an improved apparatus for the cannulation of blood vessels which is relatively easy to manufacture and has higher sensitivity than prior devices.

SUMMARY OF THE INVENTION

The present invention provides a flow monitor and vascular access system having a continuously variable frequency control. The disclosed apparatus comprises a flux panel that is capable of transmitting high power ultrasonic waves of continuously variable resonant frequencies that may be used alone with an audio monitor for sensing flow through the Doppler effect or, in the alternative, with a probe-needle assembly to receive the reflections of the panel's transmitted waves for guiding the probe-needle towards the flow.

The system of the present invention comprises three components including a flux panel, an audio monitor, and probe-needle assembly. The flux panel includes two or more sections that snap fit together through one or more hinge connections. Each of the sections may be made of a metallic conductive outer shell material having piezoelectric wafers therein. The piezoelectric wafers each have a variable thickness configuration from one end to the other. The sections of the flux panel are normally situated such that the piezoelectric wafers are arranged as diagonal opposites. An opening remains through the panel for permitting easy passage therethrough by the probe-needle assembly.

The probe-needle assembly is similar to the device disclosed in U.S. Pat. No. 4,887,606. Similarly, the audio monitor is a combined transmitting apparatus and receiving apparatus within a single housing. The transmitting apparatus portion of the audio monitor includes a variable frequency oscillator for exciting the ultrasonic transducers which are located inside the flux panel or inside the probe-needle assembly. The receiving circuit portion of the audio monitor also includes an oscillator and circuity for receiving the reflected ultrasonic waves whereby an electrical signal of audiofrequency is obtained which can be heard as an audible sound having a unique tone. The electrical components of the audio monitor are conventional and do not by themselves form any part of the present invention.

The flow monitor and vascular access system of the present invention can be operated in any one of four modes. In a monitor mode, one of the flux panel sections is connected to an output port of the audio monitor and the other section is connected to an input port. In this configuration, one of the piezoelectric wafers transmits ultrasonic waves while the other piezoelectric wafer receives the reflected waves. In this way, the flux panel and audio monitor may be used as an autonomous system for continuously monitoring flow in a vessel of interest.

In an access mode, both panel sections are connected to output ports of the audio monitor while the probe-needle assembly is connected to the input port. The flux panel sections are thus used to transmit ultrasonic waves to the entire region below them. The probe-needle assembly receives the waves echoed back from the surrounding media. The physician can use the resulting audio signal to guide him to the vessel to be accessed. Once the access is made, the panel sections can be pulled apart at the hinge connection and the probe can be removed from within the introducer needle, which permits the physician to begin the procedure intended after the vessel has been accessed by the needle. The hinge connection between the panel sections permit the sections to more easily contour the anatomical region that the panel is placed upon. Further, the panel sections may be positioned angularly with respect to each other for permitting more of the ultrasonic waves to be echoed to the receiving transducer.

In the manual monitor mode, the physician is able to set a frequency which is preferred from within a specified range for the depth of penetration required. The resonant frequency of the piezoelectric wafer is a function of its thickness. More specifically, the resonant frequency of the transducer is inversely proportional to its thickness. Since each piezoelectric wafer or transducer of the flux panel has a continuously varying thickness along its length, each portion of a respective piezoelectric wafer has a different resonant frequency. The continuously varying thicknesses of the piezoelectric transducers allow the system to be driven at various frequencies within a range whose limits are defined by the maximum and minimum thicknesses of the material. In the automatic mode, the audio monitor drives the transmitting transducers at pulses of different frequencies scaling up and down within the specified range of frequencies in a repeated sequence.

The invention described herein provides several advantages. By separating the function of transmission and reception, the transmission power in the vascular access mode is not limited to the size of a transducer in a small needle probe assembly, and therefore, the transducers in the panel sections can deliver more power and increase the depth of penetration of the transmitted and reflected waves. Further, by separating the transmission and reception, there is less interference, thereby providing cleaner signals which makes the system more sensitive. The multiple frequency capability of the system can be customized to operate at maximum performance for each anatomical situation. Similarly, the sensitivity and depth of penetration can be optimized for each specific case whether in an access mode or a monitor mode. In one of the modes, the system will repeatedly sweep across the entire spectrum of frequencies within the limits specified by the transducer thicknesses which allows the system to operate in the optimum frequency through repetitive pulses. When attempting to access a vessel, the system will allow the physician to scan in the general area of the vessel until the best signal is achieved. Effectively, the system provides a coarse "tuning" for finding the best puncture site location and a fine "tuning" for subcutaneous probing to the desired body vessel.

BRIEF DESCRIPTION OF THE DRAWINGS

FIG. 3 is another perspective view of the flux panel in an operational mode.

FIG. 4 is an end view illustrating the flux panel and probe-needle assembly in an operational mode.

FIG. 5 is a cross-sectional view of one configuration for the piezoelectric wafer.

FIG. 6 is a cross-sectional view of another configuration for the piezoelectric wafer.

FIG. 7 is a cross-sectional view of yet another configuration for the piezoelectric wafer.

DETAILED DESCRIPTION OF THE INVENTION

Figure 1:
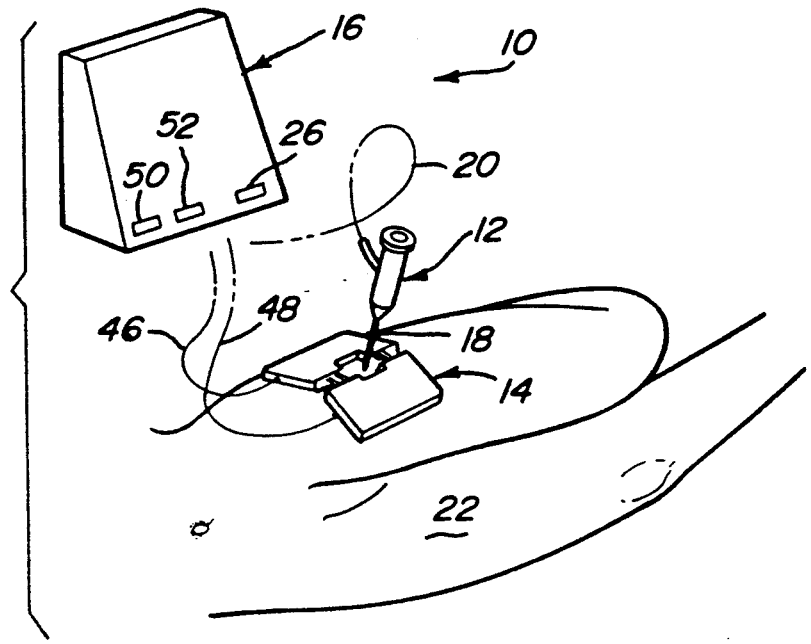
FIG. 1 is a perspective view of the flow monitor and vascular access system of the present invention.
Figure 2:
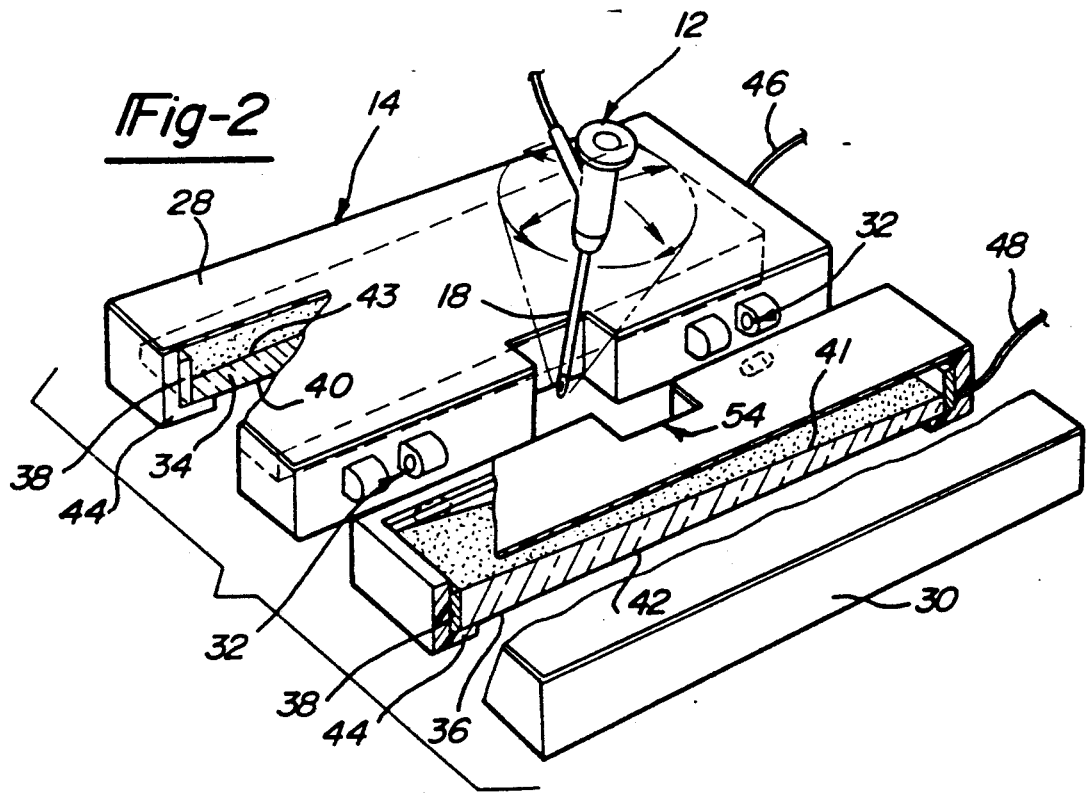
FIG. 2 is a perspective view, partly in cross-section, of the flux panel and probe-needle assembly.

With reference to FIG. 1, a schematic illustration of the flow monitor and vascular access system 10 is shown which includes a probe-needle assembly 12, a flux panel 14, and an audio monitor 16. The probe-needle assembly 12 may be made in accordance with the device disclosed in U.S. Pat. No. 4,887,606, the disclosure of which is incorporated by reference herein. The probe-needle assembly 12 includes an ultrasonic transducer means (not shown) within needle 18 at a location proximate the distal end of the needle. As is conventional, an electrical conductor 20 is connected with the transducer means within the needle for the transmission and reception of electrical signals. In the disclosed embodiment, needle 18 is inserted through tissue 22 toward a blood vessel 24 (FIG. 4). Further, the electrical connection 20 for the probe-needle assembly 12 is normally connected to the input port 26 of audio monitor 16.

The flux panel 14 is composed of at least two sections 28 and 30 which are snap fitted together at a hinge connection 32. In the disclosed embodiment, each of the sections 28 and 30 has an outer shell which may be made of a metallic conductive material. Piezoelectric wafers 34 and 36 are mounted within sections 28 and 30. Each piezoelectric wafer 34 and 36 has a continuously varying thickness from one longitudinal end to the other. The thickness across any lateral section of the wafer is uniform. A polymer inlay 38 insulates the edges of each piezoelectric wafer from the outer housing for each panel section. The piezoelectric wafers 34 and 36 are arranged relative to each other such that the thickest portion of wafer 34 is diagonally opposite from the thickest portion of wafer 36 and the thinnest portion of wafer 34 is diagonally opposite from the thinnest portion of wafer 36.

The lower or external faces 40 and 42 of the piezoelectric wafers are in electrical contact with the conductive housings for panel sections 28 and 30 through supports 44. Electrical leads 46 and 48 are connected to the output ports 50 and 52 on the audio monitor 16. Each lead 46 and 48 provides electrical connection to both the external. (40, 42) and internal (41, 43) faces of a respective piezoelectric wafer 34 or 36. Other techniques for providing electrical connection to the piezoelectric wafers are within the scope of the present invention.

When the panel sections 28 and 30 are connected together, there remains an opening 54 which is larger than the diameter of the needle-probe assembly 12 to allow easy passage of needle 18 therethrough. As shown in FIGS. 1 and 4, the probe-needle assembly 12 may be used to receive reflected ultrasonic waves that have been transmitted by piezoelectric wafers 34 and 36. During such usage, the panel sections 28 and 30 are connected by means of electrical leads 46 and 48 to the output ports 50 and 52 of audio monitor 16 and the probe-needle assembly 12 is connected by means of lead 20 to the input port 26 of audio monitor 16.

The audio monitor 16 includes both transmitting and receiving apparatus that is connected to the input and output ports 26, 50, and 52. The transmitting apparatus (not shown) is a conventional variable frequency oscillator which is used to excite the piezoelectric wafers 34 and 36 or the ultrasonic transducer within needle 18. Similarly, the receiving apparatus and related circuitry (not shown) consists of a variable frequency oscillator and related circuit for receiving the reflected ultrasonic waves and transmitting an electrical signal to a speaker or the like to produce a characteristic sound. As is conventional, the transmitted waves undergo a Doppler effect due to the movement of the corpuscles flowing through a blood vessel or the pulsation of the vascular wall, so that the reflected wave has a different frequency from that of the transmitted wave. After the reflected wave has been converted into an electrical signal with an ultrasonic oscillator, the resulting signal is sent to a speaker so that the distinctive sound can be defected by ear. The basic components of the audio monitor 16 and their operation are generally conventional. The disclosure of U.S. Pat. No. 3,556,079 is incorporated herein with respect to the conventional component used in audio monitor 16. However, the use of continuously variable frequency transmission and reception, as will be described in further detail is believed to be unique, as well as the methodology for its use as disclosed herein.

Since the power emitted by a transmitting transducer is partially a function of ills surface area, the piezoelectric wafers 34 and 36 are capable of delivery more power than the small transducer (not shown) which is housed within needle 18 and described in U.S. Pat. No. 4,887,606. This permits a significant increase in the depth of penetration of the transmitted and reflected waves. Further, by separating the function of transmission arid reception, there is not as much interference imposed on the reception of the signal due to transmission of waves from the same transducer. Moreover, because of the multiple frequency capability provided by the present invention, the system can be customized to operate at maximum performance for each anatomical situation.

Since the resonant frequency of the ultrasonic transducer is inversely proportional to its thickness, the thickest portions of the piezoelectric wafers 34 and 36 will be activated at the lowest frequency find the thinnest portions of wafers 34 and 36 will be activated at the highest frequency. For each frequency level between the lowest and highest frequencies, a different lateral band along the length of the wafers will become activated. This is schematically illustrated in FIG. 3 which shows diametrically opposed bands of activation 55 and 56. These bands of activation 55 and 56 are in response to a single frequency level. As the frequency changes, the location of activation along each wafer also changes. The unique arrangement and configuration of the piezoelectric wafers 34 and 36 of the present invention means that the ultrasonic waves are transmitted symmetrically about needle assembly 12 since each frequency excites diametrically opposite bands or portions (e.g. 55 and 56) of wafers 34 and 36. Further, by sweeping across a spectrum of frequencies, the repetitive pulses automatically result in the device operating in the optimum frequency for the specific anatomical situation. Moreover, the continuously variable frequency transmission and reception permits the physician to move the flux panel into the general area of the desired vessel until the best signal is achieved. The probe-needle 18 can then be inserted subcutaneously to access the vessel. This effectively permits coarse and fine "tuning" of the probing operation with the same system.

The flow monitor and vascular access system 10 of the present invention can be operated in any one of four modes, including a manual frequency monitor mode, an automatic frequency monitor mode, a manual frequency access mode, and an automatic frequency access mode. In the monitor mode, the probe-needle assembly 12 is not required. One of the panel sections 28 or 30 is connected to the input port 26 in the audio monitor 16 and the other panel section is connected to one of the output ports 50 or 52. In this configuration, one of the transducers 34 or 36 transmits ultrasonic waves while the other transducer receives the reflected waves as shown in FIG. 3. If the waves reflect back from a moving medium (blood flow in a vessel) the waves are thereby shifted in frequency due to the Doppler effect, which will be translated into an audible signal from the audio monitor 16. In this way, the flux panel 14 and audio monitor 16 constitute an autonomous system which can be used to continuously monitor flow in a vessel of interest. Further, because of the hinge connection 32, the two panel sections 28 and 30 can be easily positioned to the contour of the anatomical region that they are placed upon. The panel sections can be positioned to be slightly angled towards each other as shown in FIG. 3, such that more of the transmitted waves are echoed to the receiving transducer.

In the access mode, both panel transducers 34 and 36 are connected by their leads 46 and 48 to the output ports 50 and 52 of audio monitor 16 while the probe-needle assembly 12 is connected via its lead 20 to the input port 26. The piezoelectric wafers 34 and 36 are thus used to transmit ultrasonic waves to the entire region below them as shown in FIG. 4. The probe-needle assembly 12 receives the reflected waves which may be translated into an audible signal from the audio monitor 16, as previously described. The audible signal will intensify as the probe-needle assembly 12 moves into closer proximity with the desired blood vessel, thereby permitting the physician to use the audio signal to guide him to the vessel to be accessed. After access into the vessel is made, the panel sections 28 and 30 can be pulled apart at the hinge connection 32 and the probe can be removed from within the introducer needle 18. The physician can then begin the procedure intended after the vessel has been accessed by the introducer needle 18.

When the system is operated in the manual monitor mode, the physician is able to set a frequency which he prefers from within a range for the depth of penetration required. In the automatic monitor mode, the audio monitor 16 excites the transmitting transducer (either waver 34 or 36) at pulses of different frequencies thereby exciting the transmitting transducer at successive lateral sections along its length within limits defined between the thickest and thinnest portions of the piezoelectric wafer.

FIGS. 5-7 illustrate various cross sections which can be utilized for the piezoelectric wafers 34 and 36. These include a generally linear converging configuration as shown in FIG. 5, a stepped configuration as shown in FIG. 6, and a curvilinear configuration as shown in FIG. 7. The specific configuration for the cross section of the piezoelectric wafer will be depend upon such factors as the specific type of piezoelectric material and size of the panel section.

In the automatic access mode, the region underlying probe-needle assembly 12 is saturated or flooded with transmitted waves from wafers 34 and 36, as shown in FIG. 4. The diametrically opposite bands of activation (e.g. 55 and 56) are continuously moving along the lengths of opposed wafers 34 and 36 as the transmitting apparatus within audio monitor 16 sweeps across the spectrum of frequencies. After automatically scanning the general area of the vessel, the system can be stabilized to the preferred frequency for locating the best puncture site. Thus, the present invention provides a system for transmitting high powered ultrasonic waves of continuously variable resonant frequencies that may be used alone with an audio monitor for sensing flow or in conjunction with a probe-needle assembly for accessing a desired blood vessel.

Various modifications and improvements may be made to the present invention without departing from the scope thereof.

I claim:

1. An ultrasonic assembly comprising:
a flux panel having at least two sections that are movable relative to each other;
each panel section including a piezoelectric transducer; and
means for transmitting variable frequencies for activating at least one of said piezoelectric transducers; and
means for releasably and rotatably connecting said panel sections such that they may be angled relative to each other or separated from each other.

2. The ultrasonic assembly as defined in claim 1 wherein each piezoelectric transducer having a varying thickness along its length.

3. The ultrasonic assembly as defined in claim 2 wherein the thickest portion of one of said piezoelectric transducers is located at a position adjacent to the thinnest portion of the other piezoelectric transducer.

4. The ultrasonic assembly as defined in claim 1 wherein an opening is formed between said panel sections to permit access therebetween by a needle assembly.

5. An ultrasonic assembly comprising:
a flux panel and a needle assembly;
said flux panel and needle assembly each including a piezoelectric transducer; and
means for transmitting variable frequencies to at least one of said piezoelectric transducers;
said flux panel having at least two sections and an opening is formed between said panel sections to permit access therethrough by said needle assembly; and
means for releasably and rotatably connecting said panel section such that they may be angled relative to each other or separated from each other.

6. The ultrasonic assembly as defined in claim 5 wherein said flux panel having at least two piezoelectric transducers and each piezoelectric transducer of said flux panel having a varying thickness along its length.

7. The ultrasonic assembly as defined in claim 6 wherein the thickest portion of one of said flux panel piezoelectric transducers is located at a position adjacent to the thinnest portion of the other flux panel piezoelectric transducer.

8. An ultrasonic assembly comprising:
a flux panel, a needle assembly, and an audio monitor;
said flux panel and needle assembly each including a piezoelectric transducer;
said audio monitor including transmitting means for transmitting variable frequencies to one of said piezoelectric transducers for generating ultrasonic waves and said audio monitor including receiving means responsive to reflected ultrasonic waves received by the other of said piezoelectric transducers for generating an audible sound;
said flux panel having at least two sections that are movable relative to each other and each panel section including a piezoelectric transducer;
wherein an opening is formed between each panel section to permit access therethrough by said needle assembly; and
wherein means for releasably and rotatably connecting said panel sections such that they may be angled relative to each other or separated from each other.

9. The ultrasonic assembly as defined in claim 8 wherein each piezoelectric transducer of said flux panel having a varying thickness along its length.

10. The ultrasonic assembly as defined in claim 9 wherein the piezoelectric transducers of the flux panel are positioned such that the thickest portion of one piezoelectric transducer is adjacent to the thinnest portion of the other piezoelectric transducer.

11. A method for monitoring a blood vessel comprising the steps of transmitting a beam of ultrasonic sound waves into the human body from a flux panel having at least two sections that are rotatably and releasably connected and angularly movable relative to each other with each panel section including a piezoelectric transducer;
receiving reflected waves which have been changed due to the Doppler effect and converting the reflected waves into an electrical signal and reproducing it as an audible signal.

12. The method as defined in claim 11 including the step of transmitting variable frequencies to at least one of said piezoelectric transducers.

13. A method of cannulation of blood vessels comprising:
   actuating a flux panel for transmitting a beam of ultrasonic sound waves into a body toward a blood vessel wherein the flux panel including at least two sections that are rotatably and releasably connected and angularly movable relative to each other with each section including a piezoelectric transducer;
   receiving reflected waves through a receiving transducer in a needle assembly;
   converting the received waves into an electrical signal and reproducing it as an audible sound; and
   inserting the needle assembly into the body and guiding the needle assembly toward the blood vessel by adjusting the position of the needle assembly in response to the audible sound.

14. The method as defined in claim 13 including the step of transmitting variable frequencies to at least one of said flux panel piezoelectric transducers.

* * * * *